United States Patent
Kaito (10) Patent No.: US 7,167,541 B2
(45) Date of Patent: Jan. 23, 2007

(54) X-RAY PHOTOGRAPHY APPARATUS

(75) Inventor: Ryouzou Kaito, Kanagawa-ken (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 114 days.

(21) Appl. No.: 11/086,427

(22) Filed: Mar. 23, 2005

(65) Prior Publication Data
US 2005/0213707 A1   Sep. 29, 2005

(30) Foreign Application Priority Data
Mar. 23, 2004   (JP)   ............... 2004-085024

(51) Int. Cl.
*H05G 1/58* (2006.01)
(52) U.S. Cl. ............... 378/116; 378/62; 378/92
(58) Field of Classification Search ........... 378/62, 378/92, 116
See application file for complete search history.

(56) References Cited

U.S. PATENT DOCUMENTS 4,400,823 A * 8/1983 Haendle ............... 378/113
6,404,848 B1 * 6/2002 Ishisaka et al. ........... 378/62
6,426,996 B1 * 7/2002 Moribe et al. ........... 378/116
6,934,409 B1 * 8/2005 Ohara ................... 382/132
7,103,140 B1 * 9/2006 Amitani et al. ........... 378/37

FOREIGN PATENT DOCUMENTS

JP   2001-238871 A   9/2001

\* cited by examiner

*Primary Examiner*—Edward J. Glick
*Assistant Examiner*—Thomas R. Artman
(74) *Attorney, Agent, or Firm*—Sughrue Mion, PLLC (57) ABSTRACT

An X-ray photography apparatus includes a photographing system and a movement control section. The photographing system is made up of a normal X-ray source for irradiating X rays to a subject, a small focus X-ray source for irradiating X rays to the subject, and an X-ray detector for obtaining an image signal by detecting X rays transmitted through the subject. The movement control section moves and controls at least one component from among the normal X-ray source, the small focus X-ray source, and the X-ray detector so that the arrangement of the photographing system is switched between a first arrangement suitable for normal photography in which the subject is photographed employing the normal X-ray source, and a second arrangement suitable for magnified photography in which the subject is magnified and photographed, employing the small focus X-ray source.

22 Claims, 4 Drawing Sheets

SWITCHING

SWITCHING

SWITCHING

X-RAY PHOTOGRAPHY APPARATUS

BACKGROUND OF THE INVENTION

1. Field of the Invention

The present invention relates to X-ray photography apparatus, and more particularly to X-ray photography apparatus that are capable of switching between normal photography and magnified photography simply.

2. Description of the Related Art

X-ray photography has been utilized in a wide variety of fields, because it has the advantage that an X-ray image representing the interior of a subject is obtained without cutting, invasion, etc., of the subject. For example, in the field of medical diagnosis, it is common practice to take an X-ray photograph of a region (which is a diagnostic object) of a patient and inspect the obtained X-ray image for lesion regions. In various fields of industry, an X-ray photo graph of each product has been taken and the X-ray image has been inspected for defects.

Different types of X-ray sources for X-ray photography have also been developed for various uses. The examples are normal X-ray sources with a relatively large X-ray emitting surface (i.e., a relatively great focal dimension), and small focus X-ray sources with a relatively small focal dimension such as that disclosed in Japanese Unexamined Patent Publication No. 2001-238871. In normal X-ray sources, the focal dimension is great, so X-ray intensity is great and penetrating power is strong. However, this type of X-ray radiation slightly lacks uniformity in spread and X-ray images of high sharpness are hard to obtain. In small focus X-ray sources, the focal dimension is small, so X-ray intensity is small and penetrating power is weak. However, this type of X-ray radiation has excellent uniformity in spread and X-ray image of high sharpness are easy to obtain.

Typically, when taking an X-ray photograph of an object that is thick or an object that does not easily transmit X rays, X-ray intensity must be great. For example, in the field of medical diagnosis, taking a chest X ray and inspecting the chest X-ray image for lesion regions such as a mass or calcified cluster representing lung cancer have been performed. In such X-ray photography, a region whose volume is relatively large is photographed, so normal X-ray sources with great X-ray intensity are often used.

In medical image diagnosis or non-invasive inspection using X-ray images, when an observing object is relatively large compared with the entire image, for example, when the aforementioned chest X-ray image contains the mass or calcified cluster of a lung cancer, image diagnosis or inspection can be easily performed based on an X-ray image obtained by normal photography in which an X-ray photograph of the entire photographing object is taken. However, when an observing object is fine compared with the entire image, for example, when a head X-ray image contains an aneurysm in a cerebral blood vessel, an X-ray image obtained by normal photography is insufficient in sharpness and therefore sufficient observation cannot be performed.

In such a case, X-ray photography (normal photography) is first performed on the entirety of a photographing object. A region of interest is then determined in the obtained X-ray image. Next, magnified photography (e.g., X-ray photography that is performed with an X-ray source moved close to the photographing object and an X-ray detector moved away from the photographing object) is performed on a region of interest in a subject. And the obtained magnified image is observed in detail. At this time, normal photography employs a normal X-ray source and magnified photography employs a small focus X-ray source. If a normal X-ray source, as it is, is employed in magnified photography, the obtained magnified image will result in a blurred image because of a lack of uniformity in the X-ray radiation spread. However, if a small focus X-ray source is employed in magnified photography, a magnified image of high definition can be obtained, because the X-ray radiation spreads uniformly. The X-ray intensity of a small focus X-ray source is small as described above, but in the case of magnified photography, this will not cause problems, because an X-ray transmitting region in a subject becomes narrower compared with normal photography.

However, in the aforementioned method of making a switch from normal photography that employs a normal X-ray source to magnified photography that employs a small focus X-ray source, ray sources vary between normal photography and magnified photography, and the arrangement of a photographing system including a ray source and an X-ray detector, suitable for each type of photography, also varies. For that reason, the arrangement changing operation becomes troublesome and a switch between normal photography and magnified photography cannot be performed simply.

SUMMARY OF THE INVENTION

The present invention has been made in view of the aforementioned circumstances. Accordingly, it is the primary object of the present invention to provide an X-ray photography apparatus that is capable of switching between normal photography and magnified photography simply.

Note that the aforementioned Publication No. 2001-238871 discloses an X-ray photography apparatus which can simply perform both normal photography and phase image photography (photography which employs collimated monochromatic X rays obtained from a radiation X-ray source, and phase contrast photography for obtaining an edge enhanced image such as that obtained by photography, using a micro focus X-ray source which has a focal dimension of about 10 µm), but does not relate to normal photography and magnified photography.

To achieve the aforementioned object of the present invention, a first X-ray photography apparatus of the present invention includes a photographing system. The photographing system comprises three major components: (1) a normal X-ray source for irradiating X rays to a subject; (2) a small focus X-ray source for irradiating X rays to the subject; and (3) an X-ray detector for obtaining an image signal by detecting X rays transmitted through the subject. The first X-ray photography apparatus of the present invention further includes movement control means. This control means is used for moving and controlling at least one component from among the normal X-ray source, the small focus X-ray source, and the X-ray detector so that the arrangement of the photographing system is switched between a first arrangement suitable for normal photography in which the subject is photographed employing the normal X-ray source, and a second arrangement suitable for magnified photography in which the subject is magnified and photographed, employing the small focus X-ray source.

The aforementioned object of the present invention is also achieved by a second X-ray photography apparatus. The second X-ray photography apparatus of the present invention includes a photographing system. The photographing system of the second X-ray photography apparatus comprises four major components: (1) a normal X-ray source for irradiating X rays to a subject; (2) a small focus X-ray source for irradiating X rays to the subject; (3) an X-ray detector for obtaining an image signal by detecting X rays transmitted through the subject; and (4) a table for mounting the subject. The second X-ray photography apparatus of the present invention further includes movement control means. The movement control means is used to move and control at least one component from among the normal X-ray source, the small focus X-ray source, the X-ray detector, and the subject mounting table so that the arrangement of the photographing system is switched between a first arrangement suitable for normal photography in which the subject is photographed, employing the normal X-ray source and a second arrangement suitable for magnified photography in which the subject is magnified and photographed, employing the small focus X-ray source.

The aforementioned "normal X-ray source" and "small focus X-ray source" represent an X-ray source employing an X-ray tube with a first focal dimension and an X-ray source employing an X-ray tube with a second focal dimension smaller than the first focal dimension, respectively. Preferably, the focal dimension of the "normal X-ray source" is 0.3 mm to 4 mm and the focal dimension of the "small focus X-ray source" is 0.001 mm to 0.3 mm.

In the first and second X-ray photography apparatuses of the present invention, it is preferable from the viewpoints of space saving and cost reduction to employ a single X-ray detector for the normal X-ray source and small focus X-ray source, but two separate X-ray detectors may be employed.

The "X-ray detector" may employ a detector comprising a stimulable phosphor sheet (IP) and a reader, in addition to a solid state detector having photoelectric sensors arrayed on its detecting surface (FPD).

In the first X-ray photography apparatus of the present invention, an example of the case of "moving and controlling at least one component" is a case where, by preparing a normal photography system comprising a normal X-ray source and an X-ray detector, and moving only a small focus X-ray source in and out of the space between the normal X-ray source and the X-ray detector, switching is performed between the first arrangement and the second arrangement by. In this example, a subject (human body, etc.) is also moved.

In the second X-ray photography apparatus of the present invention, an example of the case of "moving and controlling at least one component" is a case where, by providing a first X-ray detector for a normal X-ray source and a second X-ray detector for a small focus X-ray source, preparing a normal photography system comprising the normal X-ray source and the first X-ray detector and a magnified photography system comprising the small focus X-ray source and the second X-ray detector, and moving and controlling only a subject mounting table between the two photographing systems, switching is performed between the first arrangement and the second arrangement.

The "first arrangement" is arrangement in which a normal X-ray source, a subject, and an X-ray detector are approximately aligned with one another, the distance between the subject and the X-ray detector is relatively short, and a small focus X-ray source is moved out of a photographing range. The "second arrangement" is arrangement in which the small focus X-ray source, the subject, and the X-ray detector are approximately aligned with one another, the distance between the small focus X-ray source and the subject is relatively short, and the normal X-ray source is moved out of the photographing range. Note that specific distances are determined by the size and configuration of a subject, the size of the detecting surface of an X-ray detector, the required sharpness in X-ray photography, etc.

In the first and second X-ray photography apparatuses of the present invention, the "movement control means" may have (1) a mechanism in which the photographing system comprising the normal X-ray source, the small focus X-ray source and the X-ray detector (or the photographing system comprising the three components and the subject mounting table) is movable within a predetermined space; (2) a driving unit for moving each component of the photographing system (e.g., a unit comprising a stepping motor and rotatable gears and wheels); and (3) a driving-unit controller for controlling the driving unit so that the components of the photographing system are moved to their respective target positions.

Each of the first and second X-ray photography apparatuses of the present invention may further include (1) image data generation means for generating normally photographed image data, based on an image signal obtained during normal photography by the X-ray detector; (2) image display means for displaying a normally photographed image represented by the normally photographed image data, based on the normally photographed image data; and (3) region-of-interest input means for inputting position information on a region of interest in the normally photographed image displayed by the image display means. In this case, the aforementioned movement control means may move and control the at least one component, based on both the position information on the region of interest and a correspondent relationship between a position on the normally photographed image and a location on an actual space that corresponds to the position, in such a way that the arrangement of the photographing system becomes an arrangement suitable for magnifying and photographing a location on the actual space that corresponds to the region of interest.

Each of the first and second X-ray photography apparatuses of the present invention may further include lesion candidate detection means for detecting a lesion candidate within the normally photographed image and acquiring position information on the lesion candidate, based on the normally photographed image data. In this case, the aforementioned image display means may display information that represents a position of the lesion candidate along with the image, based on both the image data and the position information on the lesion candidate.

The first and second X-ray photography apparatuses of the present invention may further include (1) image data generation means for generating normally photographed image data, based on an image signal obtained during normal photography by the X-ray detector; and (2) lesion candidate detection means for detecting a lesion candidate within a normally photographed image represented by the normally photographed image and acquiring position information on the lesion candidate, based on the normally photographed image data. In this case, the aforementioned movement control means may move and control the at least one component, based on both the position information on the lesion candidate and a correspondent relationship between a position on the normally photographed image and a location on an actual space that corresponds to the position, in such a way that the arrangement of the photographing system becomes an arrangement suitable for magnifying and photographing a location on the actual space that corresponds to the lesion candidate.

The first and second X-ray photography apparatuses of the present invention may further include image display means for displaying information that represents a position of the lesion candidate along with the normally photographed image, based on the normally photographed image data and the position information on the lesion candidate.

The "image display means" may be a display unit, such as a CRT display unit, for displaying a normally photographed image on the screen, or a printer for recording and displaying a normally photographed image on a recording medium such as paper.

The "region-of-interest input means" is used for inputting position information on a region of interest. For instance, when the "image display means" comprises a display unit, such as a CRT display unit, for displaying a normally photographed image on the screen, the position information on a region of interest may be input, employing input means such as a mouse, a keyboard, etc. When the "image display means" comprises a printer for recording and displaying a normally photographed image on a recording medium such as paper, the position information on a region of interest may be input, by marking a region of interest on a normally photographed image recorded and displayed on the recording medium with a pen, etc., recognizing the marked portion with a scanner, etc., and inputting position information on the recognized portion.

The "image display means" displays a normally photographed image obtained by normal photography, but may also display a magnified image obtained by magnified photography.

The "correspondent relationship between a position on the normally photographed image and a location on an actual space that corresponds to the position" can be obtained from both the positions of the normal X-ray source and X-ray detector and the correspondent relationship between a position on the detecting surface of the X-ray detector and a position on an image.

In the first and second X-ray photography apparatuses of the present invention, based on two image signals obtained during normal photography by detecting two kinds of X rays different in energy, the image data generation means may generate energy subtraction image data that represents an energy subtraction image by performing a subtraction process between two images respectively corresponding to the two image signals.

The aforementioned "energy" does not represent intensities of X rays, but represents wavelengths or frequencies of X rays. The expression "two kinds of X rays different in energy" refers to two kinds of X rays different in energy distribution.

The "energy subtraction image" is an image generated by performing a subtraction process between two images obtained by recording two kinds of X rays different in energy distribution, transmitted through a subject. For instance, when a subject is a predetermined region in a human body, the absorption spectra of X rays vary between the soft part and bone part of that region. In this case, the "energy subtraction image" is an image in which the soft part or bone part is removed or enhanced. This image is generated by photographing the subject with two kinds of X rays different in a component ratio of an energy component absorbable to soft parts and an energy component absorbable to bone parts, obtaining two images different in contrast between soft parts and bone parts, and performing a subtraction process between the two image.

The aforementioned two kinds of X rays can be obtained, for example, by varying the tube voltage of an X-ray tube. For example, the tube voltage is caused to vary to 80 kV and 120 Kv.

The aforementioned two kinds of X rays may also be X rays that respectively have energies before and after the absorption end of a contrast medium.

The expression "the absorption end of a contrast medium" refers to an energy that corresponds to a place where the absorption factor of X rays changes greatly in an X-ray absorption spectrum for the contrast medium. The expression "X rays that respectively have energies before and after the absorption end of a contrast medium" refers to X rays having an energy component just before the absorption end as its main component and X rays having an energy component just after the absorption end as its main component. For example, they are X rays having energy distribution that has a peak at an energy position just before the absorption end, and X rays having energy distribution that has a peak at an energy position just after the absorption end. Preferably, they are X rays in which 50% or greater of the energy component is contained between the absorption end and 5 keV before the absorption end, and X rays in which 50% or greater of the energy component is contained between the absorption end and 5 keV after the absorption end.

The "energy subtraction image" in the aforementioned case is, for example, an image generated by utilizing the fact that the absorption factor of X rays in a contrast medium varies greatly before and after the absorption end of the contrast medium. One example is an image in which a region injected with a contrast medium is enhanced. It is generated by photographing a subject with X rays having an energy before the absorption end and X-rays having an energy after the absorption end, obtaining two images different in contrast between a region injected with the contrast medium and a region other than that, and performing a subtraction process between the two images.

The "two kinds of X rays that respectively have energies before and after the absorption end of a contrast medium" may be monochromatic X rays.

The monochromatic X rays are X rays whose spectral band width is extremely narrow. For example, the width of the energy distribution is about 0.5 keV. Such monochromatic X rays can be obtained by dispersing normal X rays that have a relatively wide spectral band width with a spectroscope, etc.

Monochromatic X rays are high in monochromaticity, but since the energy distribution has some width and spreads at its bottom, it is not easy to cause all energy components of monochromatic X rays to be contained in a specific wavelength range. However, typically, if 80% or greater of the energy components is within the aforementioned specific wavelength range, a sufficient effect as monochromatic X rays can be obtained. Therefore, "monochromatic X rays having energies before and after the absorption end" may be X rays having 80% or greater of the energy components in the width of 0.5 eV between the absorption end and 5 keV before the absorption end, and X rays having 80% or greater of the energy components in the width of 0.5 eV between the absorption end and 5 keV after the absorption end.

In the first and second X-ray photography apparatuses of the present invention, the "image" may be an image obtained by single photography (where the number of times is not limited to once), or a sequence of images obtained by continuous photography.

Examples of the image obtained by single photography are a single image obtained by single photography, an energy subtraction image generated by performing a subtraction process between two images photographed with two kinds of X rays different in energy, etc.

Examples of the sequence of images obtained by continuous photographing are a group of images photographed at intervals of an approximately constant time, a group of images photographed by alternately emitting two kinds of X rays different in energy, and a group of energy subtraction images generated by performing a subtraction process between two images adjacent in a temporal direction, based on that group of images.

Each of the first and second X-ray photography apparatuses of the present invention may further include X-ray control means for causing the normal X-ray source to alternately irradiate the aforementioned two kinds of X rays. Based on each one of combinations of two image signals adjacent in a temporal direction obtained by the X-ray detector, the image data generation means may generate the energy subtraction image data for each of the combinations.

The expression "alternately irradiate" means that X rays different in energy are irradiated at least three times.

In this case, the image display means may arrange the aforementioned sequence of images on the screen as still images, or display the images so that they are switchable. The image display means may also display the aforementioned sequence of images as moving image, while updating them in the order of a time series.

The lesion candidate detection means may be means for detecting a lesion candidate based on the aforementioned sequence of images, or means for detecting a lesion candidate for an image selected from the aforementioned sequence of images.

Examples of the "means for detecting a lesion candidate based on the aforementioned sequence of images" are (1) means which, based on a normal image, an energy subtraction image, or these images, detects a lesion candidate within the image; and (2) means which, based on a group of images obtained by successively photographing the blood vessel of an animal injected with a contrast medium by employing a normal X-ray source, calculates time density differential for that image group and detects as a lesion candidate a singular point where this time differential exceeds a predetermined threshold value. When a lesion candidate is detected, a message indicating that a lesion candidate has been detected, an alarm with sound or voice, etc., may be output to provide adequate care.

In addition to the aforementioned method of detecting a lesion candidate based on time density differential for an image, the lesion candidate detection means may detect a lesion candidate, employing an abnormal pattern detection method, such as that described in Japanese Unexamined Patent Publication No. 2002-109510, which uses an iris filter process suitable for detecting a tumor patterns, a morphology filter process suitable for detecting a microcalcification patterns, etc.

The energy subtraction process can employ, for example, an energy subtraction method for radiation images described in Japanese Unexamined Patent Publication No. 59(1984)-083486. The photographing method that employs two kinds of X rays different in energy can employ, for example, a method applied to an high-speed photographing apparatus for energy subtraction described in Japanese Unexamined Patent Publication No. 60(1985)-225541.

The first and second X-ray photography apparatuses of the present invention has (1) a photographing system comprising a normal X-ray source, a small focus X-ray source, and an X-ray detector, or a photographing system comprising a normal X-ray source, a small focus X-ray source, an X-ray detector, and a subject mounting table; and (2) movement control means for moving and controlling some of the components of the photographing system so that the arrangement of the photographing system is switched between a first arrangement suitable for normal photography which employs the normal X-ray source and a second arrangement suitable for magnified photography which employs the small focus X-ray source. Therefore, the arrangement of the photographing system suitable for normal photography and magnified photography can be easily obtained and switching can be simply performed between normal photography and magnified photography.

The first and second X-ray photography apparatuses of the present invention are particularly suitable for diagnosing blood vessels. When a lesion candidate is detected in an X-ray image, obtained by normal photography, which represents the entirety of a region to be diagnosed, the photographing system can be immediately switched to arrangement suitable for magnified photography to photograph the detected lesion candidate, and a magnified image of high definition capable of observing the lesion candidate in detail can be obtained. Thus, the first and second X-ray photography apparatuses of the present invention are capable of enhancing inspection efficiency.

BRIEF DESCRIPTION OF THE DRAWINGS

The present invention will be described in further detail with reference to the accompanying drawings wherein.

DESCRIPTION OF THE PREFERRED EMBODIMENT

Figure 1A:
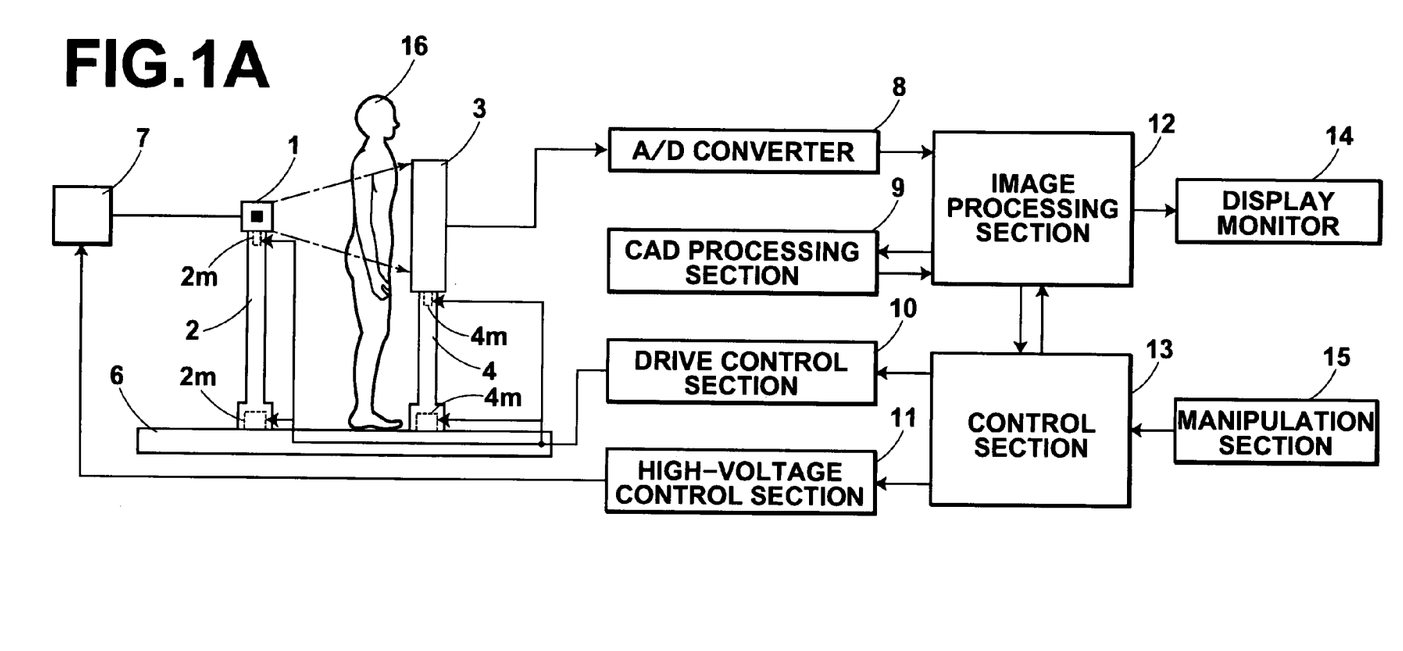
FIG. 1A is a side view showing an X-ray photography apparatus constructed in accordance with a preferred embodiment of the present invention.
Figure 1B:
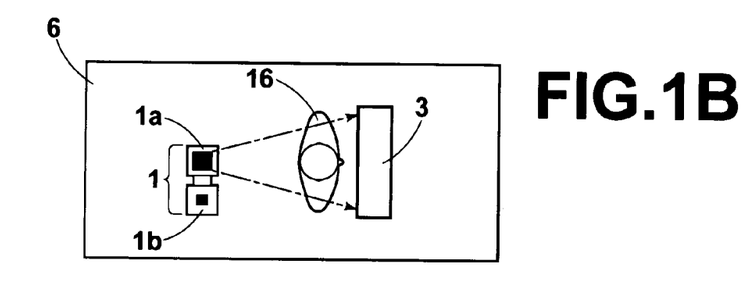
FIG. 1B is a plan view of the photographing system of the X-ray photography apparatus shown in FIG. 1A.

Referring now to FIG. 1, there is shown an X-ray photography apparatus constructed in accordance with a preferred embodiment of the present invention. The X-ray photography apparatus includes sixteen major components: (1) an X-ray source 1 comprising a normal X-ray tube (normal X-ray source) 1a whose focal dimension is about 1 mm and a small focus X-ray tube (small focus X-ray source) 1b whose focal dimension is about 0.01 mm; (2) an X-ray source supporting post 2 for supporting the normal X-ray tube 1a and small focus X-ray tube 1b so that they are arranged as one body in a horizontal direction; (3) an X-ray source driving unit 2m installed on the X-ray source supporting post 2 for driving the X-ray source 1 in the up-and-down, right-and-left, and fore-and-aft directions; (4) an X-ray detector 3 for photoelectrically detecting X rays and outputting an analog signal; (5) a detector supporting post 4 for supporting the X-ray detector 3; (6) a detector driving unit 4m installed on the detector supporting post 4 for driving the X-ray detector 4 in the up-and-down, right-and-left, and fore-and-aft directions; (7) a base plate 6 for movably supporting the X-ray source supporting post 2 and detector supporting post 4; (8) an X-ray high-voltage generator 7 connected to the X-ray source 1 for applying high voltages to the normal X-ray tube 1a and small focus X-ray tube 1b; (9) an A/D converter 8 for converting the analog signal, output from the X-ray detector 3, to a digital signal and outputting the digital signal; (10) a CAD processing section (lesion extraction means) 9 for extracting a lesion region from an image represented by image data, based on the image; (11) a drive control section 10 for driving the X-ray source driving unit 2m and detector driving unit 4m to control the positions of the X-ray source 1 and X-ray detector 3; (12) a high-voltage control section 11 for controlling voltages applied to the normal X-ray tube 1a and small focus X-ray tube 1b by the X-ray high-voltage generator 7; (13) an image processing section 12 for performing all image processing operations, such as converting the digital signal from the A/D converter 7 to image data, receiving information on the position of a lesion region extracted by the CAD processing section 9 and generating image data that corresponds to a mark indicating a lesion region, and the like; (14) a control section 13 for performing all control operations, such as controlling the drive control section 10 so that the X-ray source 1 and X-ray detector 3 are arranged at desired positions, controlling the high-voltage control section 11 so that X-ray energy and irradiation timing become desired energy and timing, and the like; (15) a display monitor 14 for receiving an image signal from the image processing section 12 and outputting the image to the screen; and (16) an operating section 15 for inputting information through a keyboard, a mouse, etc.

Note that movement control means in the present invention is made up of the X-ray source supporting post 2, detector supporting post 4, base plate 6, X-ray source driving unit 2m, detector driving unit 4m, drive control section 10, and control section 13. Image data generation means is made up of the image processing section 12 and display monitor 14. Region-of-interest input means is made up of the operating section 15 and control section 13. X-ray control means is made up of the X-ray high-voltage generator 7, high-voltage control section 11, and control section 13.

Operation of the X-ray photography apparatus shown in FIG. 1 will hereinafter be described with reference to the case of taking an X-ray photograph of the chest of a human body and detecting an aneurysm in a blood vessel of the chest.

First, a subject (human body) 16 with a blood vessel injected with an iodine contrast medium is placed at a predetermined position on the base plate 6.

Figure 2A:
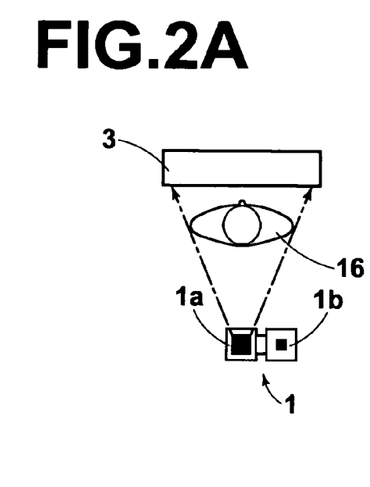
FIG. 2A is a plan view showing a first arrangement of the X-ray source and X-ray detector of the photographing system suitable for normal photography.
Figure 2B:
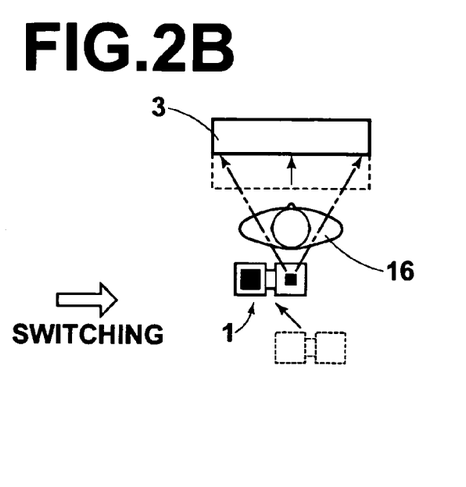
FIG. 2B is a plan view showing a second arrangement of the X-ray source and X-ray detector of the photographing system suitable for magnified photography, the second arrangement being obtained by moving the X-ray source and the X-ray detector.

If input to set a photographing mode to a normal photography mode is performed by the operating section 15, the control section 13 controls the X-ray source driving unit 2m and detector driving unit 4m by controlling the drive control section 10, and moves the X-ray source 1 and X-ray detector 3 to predetermined positions to obtain a first arrangement of the components of the photographing system suitable for normal chest photography. In the first arrangement, the normal X-ray tube 1a, the chest of the subject 16, and the X-ray detector 3 are approximately aligned with one another, the distance d1 between the normal X-ray tube 1a and the subject 16 is made longer, and the distance d2 between the subject 16 and the X-ray detector 3 is made shorter. The first arrangement suitable for normal chest photography is shown in FIG. 2A.

Figure 3:
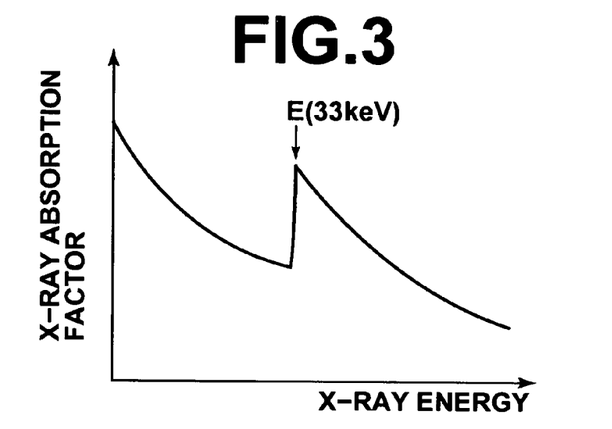
FIG. 3 is a diagram showing an overview of an X-ray absorption spectrum for an iodine contrast medium.

If input to start normal photography is performed by the operating section 15, the control section 13 controls a tube voltage that the X-ray high-voltage generator 7 applies to the normal X-ray tube 1a, by controlling the high-voltage control section 11. In this control, X rays having energies before and after the absorption end (33 keV) of the iodine contrast medium, i.e., two kinds of X rays of about 5 keV in width with energies of 30 keV and 40 keV as the respective centers are irradiated alternately and successively to the chest of the subject 16 at intervals of a fixed amount of time (e.g., 1 sec). FIG. 3 shows an over view of an X-ray absorption spectrum for an iodine contrast medium. In the figure, the absorption end of the iodine contrast medium is indicated by an arrow E.

The X-ray detector 3 photoelectrically detects X-rays transmitted through the chest of the subject 16 for each X-ray irradiation, and outputs an analog signal that corresponds to each X-ray irradiation.

The A/D converter 8 converts each analog signal, output from the X-ray detector 3, to a digital signal. Based on the digital signal, the image processing section 12 generates image data for each X-ray irradiation, i.e., each photographing and acquires successive picture frames photographed at intervals of a fixed time. The image processing section 12 further performs subtraction between each of the combinations of a odd frame and an even frame adjacent in the temporal direction; obtains an energy subtraction image, in which a region injected with an iodine contract medium is enhanced, for each combination; generates image data that corresponds to each energy subtraction image; converts the generated image data to an image signal while updating the image data in the order of a time series and sends the image signal to the display monitor 14; and causes the display monitor 14 to display the energy subtraction images on the screen as a semi moving image.

Figure 4:
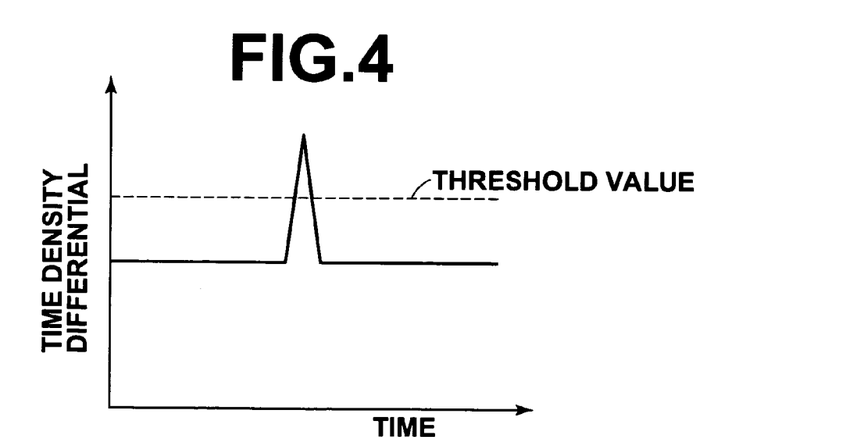
FIG. 4 is a diagram showing a singular point in time density differential for an image.

On the other hand, the CAD processing section 9 calculates time density differential (rate of temporal change) for each energy subtraction image, based on the energy subtraction image data that corresponds to each energy subtraction image, and detects as a lesion candidate a singular point where this time differential exceeds a threshold value. The reason is that there is a great possibility that a place where the flow of blood is not smooth will develop as such a singular point. An example of the singular point is shown in FIG. 4.

If a lesion candidate is detected by the CAD processing section 9, the image processing section 12 receives information on the position of the lesion candidate from the CAD processing section 9. The image processing section 12 also generates image data that represents both a mark indicating a lesion candidate on the X-ray image and a message indicating that a lesion candidate has been detected; and generates an image signal to cause the mark and message to be displayed on the screen of the display monitor 14 along with the X-ray image and sends the image signal to the display monitor 14. At this time, the display monitor 14 may output not only marks and messages, but also an alarm with sound or voice.

The X-ray photography apparatus of the preferred embodiment can set an automatic mode and a manual mode when switching the photographing system to a second arrangement suitable for magnified photography. The automatic mode is a mode in which, if a lesion candidate is detected in an X-ray image obtained by normal photography, the photographing system is switched to the second arrangement in order to take a magnified photograph of a location on an actual space corresponding to the position of the lesion candidate on the X-ray image. The manual mode is a mode in which a region of interest is manually specified in an image displayed on the screen of the display monitor 14 and the photographing system is switched to the second arrangement in order to take a magnified photograph of a location on an actual space corresponding to the position of the specified region of interest.

In the automatic mode, if a lesion candidate is detected by the CAD processing section 9, the control means 13 switches the photographing system to the second arrangement. In order to adjust the positions of the X-ray source 1 and X-ray detector 3 so that the photographing system is set in arrangement suitable for taking a magnified photograph of a location corresponding to a lesion candidate, the control means 13 further controls the drive control section 10 and changes the positions of the X-ray source 1 and X-ray detector 3, based on both the position information representing the position of a lesion candidate on an image, and the correspondent relationship between a position on an image and a location on an actual space corresponding to that position. The aforementioned correspondent relationship between a position on an image and a location on an actual space corresponding to that position can be obtained from both the positions of the normal X-ray tube 1a and X-ray detector 3 and the correspondent relationship between a position of the detecting surface of the X-ray detector 3 and a position on an image.

In the manual mode, if input to specify a region of interest in an image displayed on the screen of the display monitor 14 is performed by the operating section 15, the control means 13 controls the drive control section 10 and changes the positions of the X-ray source 1 and X-ray detector 3, in order to cause the photographing system to be set in arrangement suitable for taking a magnified photograph of a location corresponding to a region of interest, based on both the position information representing the position of a region of interest on an image and the correspondent relationship between a position on an image and a location on an actual space corresponding to that position.

FIG. 2A shows a plan view of the photographing system switched to the second arrangement in the aforementioned manner. In this example, the normal X-ray tube 1a and small focus X-ray tube 1b of the X-ray source 1 is formed as one body. In order to arrange the small focus X-ray tube 1b, a region of interest in the subject 16, and the center of the detecting surface of the X-ray detector 3 so that they are approximately aligned with one another, the X-ray source 1 is moved toward to the subject 16, while the X-ray detector 3 is moved away from the subject 16.

And if input to start magnified photography is performed by the operating section 15, the control section 13 controls a tube voltage that the X-ray high-voltage generator 7 applies to the small focus X-ray tube 1b, by controlling the high-voltage control section 11. In this manner, X rays are irradiated to the position of a lesion candidate of the subject 16.

Thereafter, as with normal photography, the image processing section 12 generates image data that represents the magnified image of a lesion candidate, based on a signal detected by the X-ray detector 3. The display monitor 14 displays the magnified image. The generated image data is transmitted to a data storage unit, incorporated in the X-ray photography apparatus of the preferred embodiment, or connected to the X-ray photography apparatus. A diagnostician can diagnose blood vessels, based on the information displayed and transmitted.

According to the X-ray photography apparatus of the present invention constructed as described above, the arrangement of the photographing system suitable for normal photography and magnified photography of a subject can be easily performed, because the photographing apparatus has the photographing system, which includes the normal X-ray source, the small focus X-ray source, and the X-ray detector, and also has movement control means for switching the arrangement of the photographing system between the first arrangement suitable for normal photography which employs the normal X-ray source and the second arrangement suitable for magnified photography which employs the small focus X-ray source, by moving some of the components of the photographing system. Therefore, it becomes possible to switch between normal photography and magnified photography simply.

In the preferred embodiment, the X-ray control means irradiates two kinds of X rays having energies before and after the absorption end of a contrast medium to a subject. In addition to this, the X-ray control means may irradiate two kinds of X rays different in a component ratio of an energy component absorbable to soft parts of a human body and an energy component absorbable to bones. In this case, two images of a soft part and a bone part different in contrast can be obtained. An energy subtraction image, generated by performing a subtraction process between the two images, is an image from which soft parts or bone parts are removed. Therefore, this energy subtraction image can be utilized in observing only soft parts or only bone parts.

The X-ray control means may also irradiate a single kind of X ray having the same energy successively. In this case, the image processing section 12 may generate an image, obtained by each photographing, as image data without performing a subtraction process.

The X-ray control means may perform X-ray irradiation once or a predetermined number of times at a time.

In the preferred embodiment, the image display means displays a sequence of images, successively photographed, as a so-called semi moving image, while updating them in the order of a time series. In addition to this, the image display means may arrange the aforementioned sequence of images on the screen as still images. It may also display the images so that they are switchable.

In the preferred embodiment, the lesion candidate detection means extracts as a lesion candidate a singular point where time density differential for an image exceeds a predetermined threshold value. In addition to this, the lesion candidate detection means may detect a lesion candidate, employing an abnormal pattern detection method, such as that disclosed in the aforementioned Japanese Unexamined Patent Publication No. 2002-109510, which uses an iris filter process suitable for detecting a tumor pattern, a morphology filter process suitable for detecting microcalcification patterns, etc.

Figure 5A:
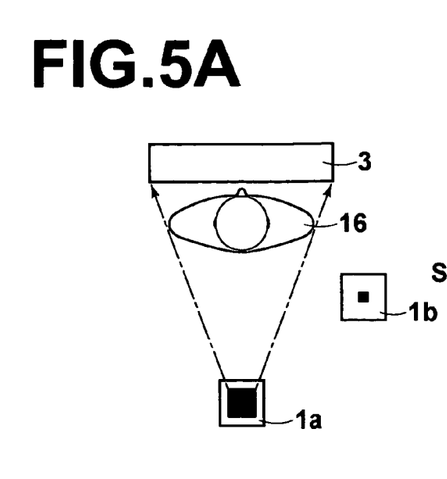
FIG. 5A is a plan view showing a first arrangement of the normal X-ray tube, laterally movable small focus X-ray tube, and X-ray detector of the photographing system suitable for normal photography.
Figure 5B:
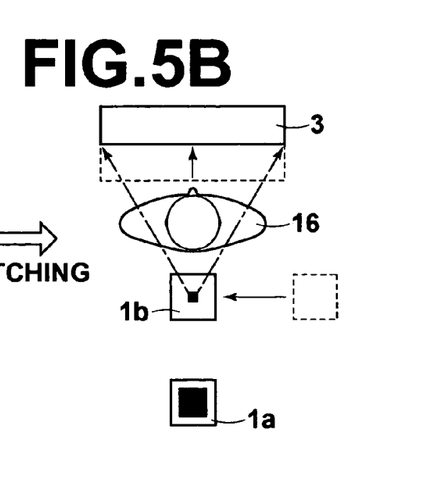
FIG. 5B is a plan view showing a second arrangement of the normal X-ray tube, laterally movable small focus X-ray tube, and X-ray detector of the photographing system suitable for magnified photography, the second arrangement being obtained by moving the laterally movable small focus X-ray tube horizontally and the X-ray detector.
Figure 6A:
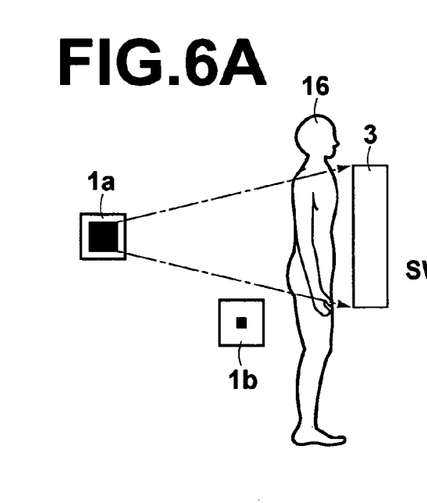
FIG. 6A is a side view showing a first arrangement of the normal X-ray tube, vertically movable small focus X-ray tube, and X-ray detector of the photographing system suitable for normal photography.
Figure 6B:
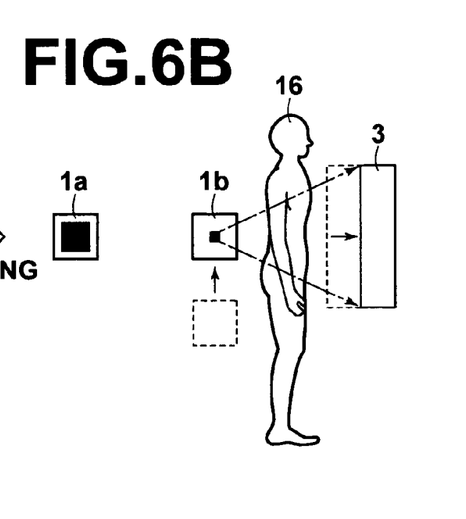
FIG. 6B is a side view showing a second arrangement of the normal X-ray tube, vertically movable small focus X-ray tube, and X-ray detector of the photographing system suitable for magnified photography, the second arrangement being obtained by moving the vertically movable small focus X-ray tube horizontally and the X-ray detector.

In the preferred embodiment, the movement control means switches the photographing system between normal photography and magnified photography, by moving the X-ray source 1 (in which the normal X-ray tube 1a and the small focus X-ray tube 1b are formed as one body) and the X-ray detector 3. In addition to this, the normal X-ray tube 1a and the small focus X-ray tube 1b may be separately supported, as shown in FIGS. 5 and 6. In this case, the photographing system may be switched between normal photography and magnified photography, by moving the small focus X-ray tube 1b and X-ray detector 3.

Figure 7A:
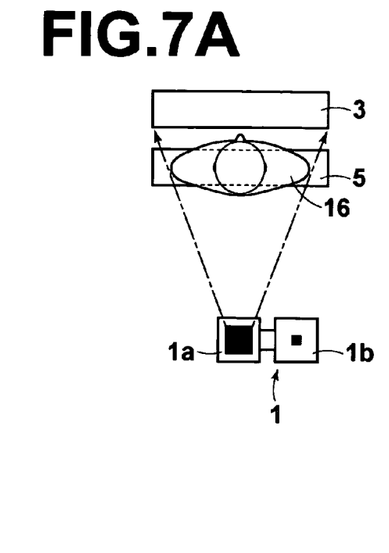
FIG. 7A is a plan view showing a first arrangement of the X-ray source, subject mounting table, and X-ray detector of the photographing system suitable for normal photography.
Figure 7B:
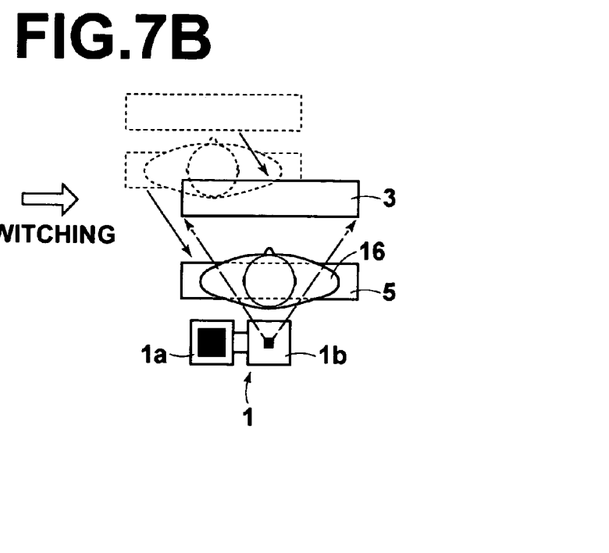
FIG. 7B is a plan view showing a second arrangement of the X-ray source, subject mounting table, and X-ray detector of the photographing system suitable for magnified photography, the second arrangement being obtained by moving the subject mounting table and the X-ray detector.
Figure 8A:
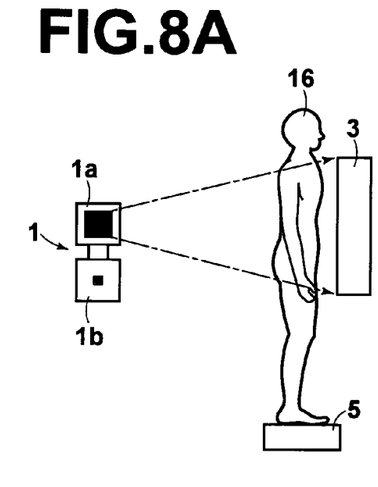
FIG. 8A is a side view showing a first arrangement of the X-ray source, subject mounting table, and X-ray detector of the photographing system suitable for normal photography.
Figure 8B:
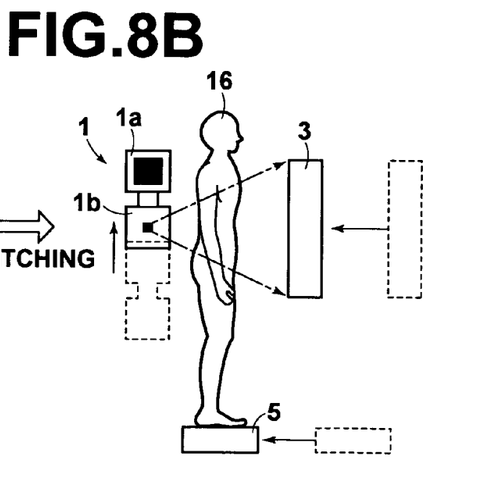
FIG. 8B is a side view showing a second arrangement of the X-ray source, subject mounting table, and X-ray detector of the photographing system suitable for magnified photography, the second arrangement being obtained by moving the X-ray source, the subject mounting table, and the X-ray detector.

In the preferred embodiment, the photographing system includes the normal X-ray tube 1a, the small focus X-ray tube 1b, and the X-ray detector 3. The photographing system may further include a table 5 for mounting the subject 16. In this case, switching of the photographing system may be performed by moving the subject mounting table 5 and X-ray detector 3, as shown in FIG. 7, or by moving the X-ray source 1 and X-ray detector 3, as shown in FIG. 8.

In the case where a plurality of lesion candidates are detected, any of them may be selected. In this case, the components of the photographing system are arranged so that they are suitable for taking a magnified photograph of a location on an actual space that corresponds to the selected lesion candidate. Also, among a plurality of lesion candidates, a lesion candidate in which a change in the aforementioned time density differential is greatest may be preferentially specified. In this case, the components of the photographing system are arranged so that they are suitable for taking a magnified photograph of a location on an actual space that corresponds to the specified lesion candidate. Furthermore, in the specified order of a candidate group or in the higher order of a lesion probability, the components of the photographing system may be previously programmed so as to be arranged so that they are suitable for taking a magnified photograph of a location on an actual space that corresponds to each lesion candidate.

What is claimed is:

1. An X-ray photography apparatus comprising:
  a photographing system comprising
    a normal X-ray source for irradiating X rays to a subject,
    a small focus X-ray source for irradiating X rays to said subject, and
    an X-ray detector for obtaining an image signal by detecting X rays transmitted through said subject; and
  movement control means for moving and controlling at least one component from among said normal X-ray source, said small focus X-ray source, and said X-ray detector so that the arrangement of said photographing system is switched between a first arrangement suitable for normal photography in which said subject is photographed employing said normal X-ray source, and a second arrangement suitable for magnified photography in which said subject is magnified and photographed, employing said small focus X-ray source.

2. The X-ray photography apparatus as set forth in claim 1, further comprising
  image data generation means for generating normally photographed image data, based on an image signal obtained in said normal photography by said X-ray detector;
  image display means for displaying a normally photographed image represented by said normally photographed image data, based on said normally photographed image data; and
  region-of-interest input means for inputting position information on a region of interest in said normally photographed image displayed by said image display means;
  wherein said movement control means moves and controls said at least one component, based on both said position information on said region of interest and a correspondent relationship between a position on said normally photographed image and a location on an actual space that corresponds to said position, in such a way that the arrangement of said photographing system becomes an arrangement suitable for magnifying and photographing a location on the actual space that corresponds to said region of interest.

3. The X-ray photography apparatus as set forth in claim 2, further comprising
  lesion candidate detection means for detecting a lesion candidate on said normally photographed image and acquiring position information on said lesion candidate, based on said normally photographed image data;
  wherein said image display means displays information that represents a position of said lesion candidate along with said image, based on both said image data and said position information on said lesion candidate.

4. The X-ray photography apparatus as set forth in claim 2, wherein, based on two image signals obtained in said normal photography by detecting two kinds of X rays different in energy, said image data generation means performs a subtraction process between two images respectively corresponding to said two image signals and generates energy subtraction image data that represents an energy subtraction image.

5. The X-ray photography apparatus as set forth in claim 3, wherein, based on two image signals obtained in said normal photography by detecting two kinds of X rays different in energy, said image data generation means performs a subtraction process between two images respectively corresponding to said two image signals and generates energy subtraction image data that represents an energy subtraction image.

6. The X-ray photography apparatus as set forth in claim 5, wherein said two kinds of X rays are X rays that respectively have energies before and after an absorption end of a contrast medium.

7. The X-ray photography apparatus as set forth in claim 5, further comprising
X-ray control means for causing said normal X-ray source to alternately irradiate said two kinds of X rays;
wherein, based on each of combinations of two image signals adjacent in a temporal direction obtained by said X-ray detector, said image data generation means generates said energy subtraction image data for each of said combinations.

8. The X-ray photography apparatus as set forth in claim 6, further comprising
X-ray control means for causing said normal X-ray source to alternately irradiate said two kinds of X rays;
wherein, based on each of combinations of two image signals adjacent in a temporal direction obtained by said X-ray detector, said image data generation means generates said energy subtraction image data for each of said combinations.

9. The X-ray photography apparatus as set forth in claim 1, further comprising
image data generation means for generating normally photographed image data, based on an image signal obtained in said normal photography by said X-ray detector; and
lesion candidate detection means for detecting a lesion candidate on a normally photographed image represented by said normally photographed image and acquiring position information on said lesion candidate, based on said normally photographed image data;
wherein said movement control means moves and controls said at least one component, based on both said position information on said lesion candidate and a correspondent relationship between a position on said normally photographed image and a location on an actual space that corresponds to said position, in such away that the arrangement of said photographing system becomes an arrangement suitable for magnifying and photographing a location on the actual space that corresponds to said lesion candidate.

10. The X-ray photography apparatus as set forth in claim 9, further comprising image display means for displaying information that represents a position of said lesion candidate along with said normally photographed image, based on said normally photographed image data and said position information on said lesion candidate.

11. The X-ray photography apparatus as set forth in claim 9, wherein, based on two image signals obtained in said normal photography by detecting two kinds of X rays different in energy, said image data generation means performs a subtraction process between two images respectively corresponding to said two image signals and generates energy subtraction image data that represents an energy subtraction image.

12. An X-ray photography apparatus comprising:
a photographing system comprising
a normal X-ray source for irradiating X rays to a subject,
a small focus X-ray source for irradiating X rays to said subject,
an X-ray detector for obtaining an image signal by detecting X rays transmitted through said subject, and
a table for mounting said subject; and
movement control means for moving and controlling at least one component from among said normal X-ray source, said small focus X-ray source, said X-ray detector, and said subject mounting table so that the arrangement of said photographing system is switched between a first arrangement suitable for normal photography in which said subject is photographed employing said normal X-ray source, and a second arrangement suitable for magnified photography in which said subject is magnified and photographed, employing said small focus X-ray source.

13. The X-ray photography apparatus as set forth in claim 12, further comprising
image data generation means for generating normally photographed image data, based on an image signal obtained in said normal photography by said X-ray detector;
image display means for displaying a normally photographed image represented by said normally photographed image data, based on said normally photographed image data; and
region-of-interest input means for inputting position information on a region of interest in said normally photographed image displayed by said image display means;
wherein said movement control means moves and controls said at least one component, based on both said position information on said region of interest and a correspondent relationship between a position on said normally photographed image and a location on an actual space that corresponds to said position, in such a way that the arrangement of said photographing system becomes an arrangement suitable for magnifying and photographing a location on the actual space that corresponds to said region of interest.

14. The X-ray photography apparatus as set forth in claim 13, further comprising
lesion candidate detection means for detecting a lesion candidate on said normally photographed image and acquiring position information on said lesion candidate, based on said normally photographed image data;
wherein said image display means displays information that represents a position of said lesion candidate along with said image, based on both said image data and said position information on said lesion candidate.

15. The X-ray photography apparatus as set forth in claim 13, wherein, based on two image signals obtained in said normal photography by detecting two kinds of X rays different in energy, said image data generation means performs a subtraction process between two images respectively corresponding to said two image signals and generates energy subtraction image data that represents an energy subtraction image.

16. The X-ray photography apparatus as set forth in claim 14, wherein, based on two image signals obtained in said normal photography by detecting two kinds of X rays different in energy, said image data generation means performs a subtraction process between two images respectively corresponding to said two image signals and generates energy subtraction image data that represents an energy subtraction image.

17. The X-ray photography apparatus as set forth in claim 16, wherein said two kinds of X rays are X rays that respectively have energies before and after an absorption end of a contrast medium.

18. The X-ray photography apparatus as set forth in claim 16, further comprising
X-ray control means for causing said normal X-ray source to alternately irradiate said two kinds of X rays;
wherein, based on each of combinations of two image signals adjacent in a temporal direction obtained by said X-ray detector, said image data generation means generates said energy subtraction image data for each of said combinations.

19. The X-ray photography apparatus as set forth in claim 17, further comprising X-ray control means for causing said normal X-ray source to alternately irradiate said two kinds of X rays;

wherein, based on each of combinations of two image signals adjacent in a temporal direction obtained by said X-ray detector, said image data generation means generates said energy subtraction image data for each of said combinations.

20. The X-ray photography apparatus as set forth in claim 12, further comprising image data generation means for generating normally photographed image data, based on an image signal obtained in said normal photography by said X-ray detector; and lesion candidate detection means for detecting a lesion candidate on a normally photographed image represented by said normally photographed image and acquiring position information on said lesion candidate, based on said normally photographed image data;

wherein said movement control means moves and controls said at least one component, based on both said position information on said lesion candidate and a correspondent relationship between a position on said normally photographed image and a location on an actual space that corresponds to said position, in such a way that the arrangement of said photographing system becomes an arrangement suitable for magnifying and photographing a location on the actual space that corresponds to said lesion candidate.

21. The X-ray photography apparatus as set forth in claim 20, further comprising image display means for displaying information that represents a position of said lesion candidate along with said normally photographed image, based on said normally photographed image data and said position information on said lesion candidate.

22. The X-ray photography apparatus as set forth in claim 20, wherein, based on two image signals obtained in said normal photography by detecting two kinds of X rays different in energy, said image data generation means performs a subtraction process between two images respectively corresponding to said two image signals and generates energy subtraction image data that represents an energy subtraction image.

* * * * *